(12) United States Patent
Blackwell et al.

(10) Patent No.: US 7,001,932 B2
(45) Date of Patent: Feb. 21, 2006

(54) DENTAL COMPOSITE RESTORATIVE MATERIAL AND METHOD OF RESTORING A TOOTH

(75) Inventors: Gordon B. Blackwell, Constance (DE); Karin Utz, Constance (DE)

(73) Assignee: Dentsply DeTrey GmbH, Constance (DE)

(*) Notice: Subject to any disclaimer, the term of this patent is extended or adjusted under 35 U.S.C. 154(b) by 157 days.

(21) Appl. No.: 10/732,969

(22) Filed: Dec. 11, 2003

(65) Prior Publication Data

US 2004/0122127 A1    Jun. 24, 2004

Related U.S. Application Data

(63) Continuation-in-part of application No. 09/978,741, filed on Oct. 16, 2001, now abandoned, which is a continuation-in-part of application No. 09/540,389, filed on Mar. 31, 2000, now Pat. No. 6,306,927.

(60) Provisional application No. 60/128,734, filed on Apr. 12, 1999.

(51) Int. Cl.
*A61K 6/08* (2006.01)

(52) U.S. Cl. ............... 523/116; 523/115; 523/220; 523/223; 106/35; 433/228.1

(58) Field of Classification Search ........ 523/115–116, 523/220, 223; 106/35; 433/228.1
See application file for complete search history.

(56) References Cited

U.S. PATENT DOCUMENTS

| | | | |
|---|---|---|---|
| 3,740,850 A | 6/1973 | Bowen et al. ............... 32/15 |
| 3,801,344 A | 4/1974 | Dietz .................... 106/300 |
| 4,215,033 A | 7/1980 | Bowen .................. 260/42.15 |
| 4,243,578 A | 1/1981 | O'Sullivan et al. ...... 260/42.52 |
| 4,297,266 A | 10/1981 | Ibsen et al. ............. 260/42.14 |
| 4,374,937 A | 2/1983 | Nemcek et al. ............ 523/116 |
| 4,386,912 A | 6/1983 | Nagase et al. ............. 433/228 |
| 4,388,069 A | 6/1983 | Orlowski .................. 433/228 |
| 4,407,984 A | 10/1983 | Ratcliffe et al. ............ 523/115 |
| 4,427,799 A | 1/1984 | Orlowski et al. ............ 523/116 |
| 4,454,258 A | 6/1984 | Kawahara et al. ........... 523/116 |
| 4,459,193 A | 7/1984 | Ratcliffe et al. ......... 204/159.23 |
| 4,504,231 A | 3/1985 | Koblitz et al. .............. 433/228 |
| 4,544,359 A | 10/1985 | Waknine .................... 523/115 |
| 4,572,920 A | 2/1986 | Rawls et al. ............... 523/115 |
| 4,649,165 A | 3/1987 | Kuhlmann .................. 523/116 |
| 5,192,815 A | 3/1993 | Okada et al. ............... 523/115 |
| 5,228,907 A | 7/1993 | Eppinger et al. ............. 106/35 |
| 5,244,933 A | 9/1993 | Eidenbenz et al. ............ 522/3 |
| 5,319,014 A | 6/1994 | Moorman et al. ........... 524/427 |
| 5,350,782 A | 9/1994 | Sasaki et al. ............... 523/116 |
| 5,356,951 A | 10/1994 | Yearn et al. ................ 523/116 |
| 5,730,601 A | 3/1998 | Bowman et al. ......... 433/228.1 |
| 5,856,374 A | 1/1999 | Ono et al. .................. 523/116 |
| 6,306,927 B1 | 10/2001 | Blackwell et al. .......... 523/116 |

FOREIGN PATENT DOCUMENTS

| | | |
|---|---|---|
| EP | 0 026 398 | 4/1981 |
| EP | 0 053 442 | 6/1982 |
| EP | 0 060 911 | 9/1982 |
| EP | 0 530 926 | 3/1993 |
| EP | 0 717 976 | 6/1996 |
| GB | 1 544 776 | 4/1979 |
| WO | 81/02254 | 8/1981 |
| WO | 92/12698 | 8/1992 |
| WO | 95/06453 | 3/1995 |
| WO | 98/36729 | 8/1998 |
| WO | 98/43596 | 10/1998 |
| WO | 00/03688 | 1/2000 |
| WO | 00/61073 | 10/2000 |

*Primary Examiner*—Peter Szekely
(74) *Attorney, Agent, or Firm*—Douglas J. Hura; James B. Bieber; Daniel W. Sullivan

(57) ABSTRACT

A composite material is provided which, while having an unusually high filler content may be extruded from a dental syringe and remains easily adaptable in the dental cavity. When materials of the present invention are cured, dental restorations are provided which have unusually high surface hardness and yield strength, as well as a low volume shrinkage on curing. This is achieved by use of a mixture of filler particles with a specific size, size range, and size relationship. Such a combination of properties makes the material of the present invention particularly useful for restoring cavities in posterior teeth.

6 Claims, No Drawings

DENTAL COMPOSITE RESTORATIVE MATERIAL AND METHOD OF RESTORING A TOOTH

RELATED APPLICATION

This application is a continuation-in-part of pending application U.S. Ser. No. 09/978,741, which is a continuation-in-part of U.S. Ser. No. 09/632,065 now issued as U.S. Pat. No. 6,306,927.

BACKGROUND TO THE INVENTION

Dental composites, which essentially comprise a mixture of a polymerisable resin and a glassy filler, have been developing since the early 1970's, when the first materials of this class were introduced. See for example R. L. Bowen et al., "A new series of X-ray-opaque reinforcing fillers for composite materials, J. Dental Research, vol. 51(1) 1972. Until this time, fillings had been based on silver-mercury amalgams, mixtures of acid leachable glass with phosphoric acid (known as "silicate cements"), or unfilled polymerisable resins, and each class of material has certain strengths and weaknesses. For instance, amalgams are generally considered to be cheap and easy to use, and to have a long life time due to their strength and high resistance to wear. Disadvantages of amalgam are toxicity of the mercury and the black colour of the filling. Silicate fillings were approximately tooth coloured and released fluoride into the tooth to help prevent a recurrence of decay. However they tended to dissolve quickly and were weak, and are barely used nowadays. Unfilled resins brought advantages of toughness, convenience, and aesthetics, but were still weak, limiting their use to areas of low stress. These unfilled resins also have a high volume shrinkage, commonly at least 5%. This leads to formation of gaps between the filling and the tooth, and subsequent recurring decay of the tooth around and underneath the restoration. The introduction of composite materials brought improvements in surface hardness, higher physical strengths, good aesthetics, lower shrinkage, and also higher resistance to wear. However the wear rate of these composite materials is still higher than that of amalgam, and their shrinkage of around 2 to 3 volume percent still leads to gap formation and recurrent caries. It is an aim of many researchers in the dental area to develop composite materials with higher strength, reduced shrinkage and higher resistance to wear, which may be used in place of amalgam. Preferably the material should also be extrudable from a dental syringe since this procedure is not only convenient and time saving for the dentist, but also helps to avoid the inclusion of air bubbles in the cavity.

The present invention provides composite materials with low shrinkage and high surface hardness, and a method for preparing these composite materials. Within certain ranges of the invention materials are provided which may also be extruded from a dental syringe designed for this use.

Composite materials for dental use and general methods for making them have been known for many years. See for example BP1401805, U.S. Pat. No. 3,740,850, U.S. Pat. No. 4,215,033, and U.S. Pat. No. 3,801,344. These patents essentially describe mixtures of acrylate resins with glass or various metal oxides as filler and claim, for example, the advantages of natural colour and desirable hardness. Although an improvement at the time, these early materials were still relatively week and had low resistance to wear. Improvements in surface hardness were achieved when milling procedures improved and fillers with smaller particle sizes became available. Attempts were also made to use different types of monomer, for instance a silane containing monomer as in U.S. Pat. No. 4,504,231, or a mixture of monomers as in U.S. Pat. No. 5,730,601. However the shrinkage of these materials still remained too high, at around 2 to 3 percent by volume. Further improvements were made by the inclusion of two or more types of filler particle, for example a conventional glass fillers with particle size ranges of 0.5 to 40 microns and 0.2 to 15 microns, together with a fine filler with particle size in the range 5 to 150 nano meters, as in U.S. Pat. No. 4,649,165. These materials however still have the problem that it is hard to incorporate sufficient filler into the composite to obtain the desired hardness. Attempts to overcome this problem have also included the use of surfactants, as in U.S. Pat. No. 4,374,937. However there remains the problem that use of too much conventional filler material in a composite leads to a stiff paste which is hard to manipulate, and ultimately to a dry and non-cohesive mixture. It is desirable to be able to extrude a dental filling material directly from a syringe into the tooth cavity, and this is not possible with such stiff pastes. Such pastes when cured typically have a yield strength around 130 MPa, a surface Vickers hardness of about 70, and a volume shrinkage between 2.5 to 3 percent. The yield strength is the maximum load that may be applied to a material before permanent deformation and damage occurs, and it is desirable that this is a high as possible. A high surface hardness is needed because this reduces abrasive wear of the material, while low shrinkage is desirable in order to minimise gap formation around a filling.

DETAILED DESCRIPTION OF THE INVENTION

In the present invention it has been found that by the use of filler combinations with a certain defined size distribution and size relationship, an unexpectedly high amount of filler may be combined with the resin matrix without the paste becoming either stiff and hard to handle, or crumbly and non-cohesive. The resulting pastes when cured have a yield strength of at least 180 MPa, a Vickers hardness of about 90, and a volume shrinkage on curing less than 2%. A conventionally made composite paste commonly contains ground glass particles with a particle distribution of about 0.05 to 1 micron together with small amounts of a siliceous filler with a particle size distribution between about 0.01 and 0.1 microns. This latter is added to adjust the handling properties of the paste. The total amount of filler contained in such a composition to give a consistency which is clinically useful is commonly around 75%, but may be as high as about 80% in some cases. Typical physical properties are a yield strength around 130 MPa, a Vickers hardness around 70, and shrinkage on cure of about 2.5 to 3.0%. The Shore A hardness of the uncured paste is used as a measure of "packability" and "handling characteristics" of the paste, and it has been determined empirically that for filling materials which are to be used in posterior cavities an optimum value for the Shore A hardness is between about 50 and 55. A paste made as above typically has a Shore A hardness of around 30 to 45. In the present invention, a paste as above is taken and mixed with an additional fraction of filler chosen such that the mean particle size of this additional filler is at least about twenty times the mean size of the first filler in the paste, and is preferably essentially monomodal. The particle size distribution of a powder is conveniently indicated by the span, which is defined as (D(v, 0.9)−D(v, 0.1))/D(v, 0.5) where D(v, 0.5) is the mean particle size with 90% of the particles smaller than D(v, 0.9) and 10% of the particles smaller than D(v, 0.1). In practice the particle size of the additional filler will have a distribution, but the span as defined above should be as small as possible and should preferably be less than about 1.3. Thus in the above example, the mean particle size of the glass (first filler) contained in the paste is 0.8 micron, and the mean size of the additional filler should therefore be at least about 16 microns, with no more than 10% of the particles either larger than 27 microns or smaller than 5 microns. However, the additional filler may also be larger, for example with a mean size of about 65 microns. In this case the D(v, 0.9) should not be larger than 115 microns, and the D(v, 0.1) and the D(v, 0.1) should not be smaller than 16 microns. Such a filler fraction may conveniently be made by passing milled glass through commercially available sieves.

Therefore, according to the present invention an intra-oral or extra-oral dental restorative material includes at least on polymerisable monomer, a first solid filler component with a mean particle size between 0.1 and 5 microns, a second solid filler component with a mean particle size at least ten times greater than the mean particle size of the first solid filler component and a particle size span of less than 1.5.

Another preferred embodiment of the invention includes a similar material wherein the second solid filler component has a mean particle size at least twenty times greater than the mean particle size of the first solid filler component. The particle size span of the second filler component may also be less than 1.3.

According to another embodiment of the invention, about 70% of the particles in the second filler component are within the range of 75 to 125 percent of its mean size. In another embodiment, at least 80 percent of the particles in the second filler component are within that range.

A preferred material also includes from about 5 to 25 percent by weight of the polymerisable component, or more preferably from about 10 to 15 percent by weight of that component.

The Vickers hardness of such a cured material according to the present invention is preferably greater than 80 and the yield strength is at least 180 MPa. The Vickers hardness may also be greater than 90.

One of the solid filler components may include a fluoride containing glass or spherical or essentially spherical particles or fluoride containing glass particles.

The material also may contain between 0 and about 5 percent of a solid filler having a mean particle size of from about 1 to 100 nm.

When the material according to the present invention is extruded from a syringe or a dental syringe with a tip diameter of 2 mm, the extrusion force is preferably less than about 300 Newtons.

The following examples serve to illustrate the invention further, but are not restrictive in any way. Since the materials described in the examples are sensitive to and hardened by exposure to light between 400 and 500 nm, all preparations were done in yellow light devoid of light in this wavelength range. In the following examples "parts" means "parts by weight".

EXAMPLE 1

Preparation of the Initial Paste

A resin mixture was first made by combining urethane resin 44 parts, TCB resin 34 parts, trimethylolpropane trimethacrylate 20 parts, camphor quinone 0.28 parts, dim- ethylaminobenzoic acid ethyl ester 0.59 parts, butylated hydroxytoluene 0.1 parts, hydroquinone monomethylether 0.025 parts, and 2-hydroxy-4-methoxybenzophenone 1.0 part in a flask and stirring at 50° C. until a clear homogenous mixture was obtained.

This resin (25.3 parts) was then mixed at 50° C. with 74.7 parts of a powder mixture comprising silanated strontium glass with a mean particle size of 0.8 microns and a span as defined above of 1.6 94.5 parts, strontium fluoride 5 parts, and hydrophobic fumed silica (particle size range about 0.05 microns) 0.5 parts, to give a stiff paste after cooling. The overall filler content of this paste is 74.7% by weight. The properties of this paste were measured and results are given in Table 1

EXAMPLE 2

Preparation of a the Addition Filler with Narrow Particle Size Distribution

Glass frit with a particle size of about 2 to 5 mm was milled in a dry ball mill to give a powder with a particle size ranging from about 1 micron to 1 mm and a mean particle size of about 50 microns. This was sieved over a mesh with an aperture size of 250 microns, and the coarse fraction remaining in the sieve was discarded. The glass which passed through was sieved over a mesh with an aperture or 100 microns to obtain a fraction with a particle range between 100 and 250 microns and a span of about 0.9. This is termed fraction A. The remaining glass was sieved over a mesh with an aperture of 85 microns, and the glass remaining in the sieve was discarded. The glass which passed through was collected and sieved over a mesh with an aperture size of 48 microns, the fraction which passed through being discarded. In this way a fraction with a particle size range of 48 to 85 microns was obtained. This is termed fraction B. Both fractions A and B were separately silanated by slurrying them at room temperature with 3-(trimethoxysilyl)propyl methacrylate (1% of the weight of the glass) dissolved in water acidified with acetic acid. After one hour the glass fractions were filtered off and dried for 18 hours at 85° C. in an oven. When the particle size of fraction B was measured using a Malver Mastersizer S ver 2.10, the mean particle size was shown to be about 60 microns, with a D(0.9) of 89.5 microns and a D(0.1) of 14.2 microns.

This corresponds to a span of 1.26

EXAMPLE 3

Preparation of a First Paste Containing Additional Filler Fraction B

UK221581

Two hundred grams of the paste from example 1 was taken and mixed at 50° C. with 160 grams of silanated glass fraction B from example 2 using a planetary mixer. After mixing for 15 minutes the paste had formed a coherent mass. This was cut up and was spread around the mixing pot before being mixed for a further 15 minutes. The paste mass was again cut up, spread around the pot and mixed for 15 minutes, but this time a vacuum of 220 mbar was applied for the last 10 minutes. The resulting paste when cool was only marginally stiffer than the original paste from example 1 even though it contained a total of 86% filler by weight. The properties of the paste were measured and these are given in Table 1.

EXAMPLE 4

Preparation of a Second Paste Containing Additional Filler Fraction B

UK221591

The paste from example 3 (342 grams) was taken and 13 grams of silanated glass from example 2 fraction B was added using the procedure as given in example 3. This paste contained a total of 86.5% filler. The properties were measured and results are given in Table 1.

EXAMPLE 5

Preparation of a Third Paste Containing Additional Filler Fraction B

UK221592

Paste from example 4 (293 grams) was taken and 12 grams of silanated glass from example 2 fraction B was added using the procedure as given in example 3. This paste contained a total of 87.0% filler. The properties were measured and results are given in Table 1.

EXAMPLE 6

Preparation of a Fourth Paste Containing Additional Filler Fraction B

UK221592

Paste from example 5 (265 grams) was taken and 10 grams of silanated glass from example 2 fraction B was mixed in using the procedure as given in example 3. This paste contained a total of 87.5% filler. The properties were measured and results are given in Table 1.

EXAMPLE 7

Preparation of a Fifth Paste Containing Additional Filler Fraction B

UK221593

Paste from example 6 (235 grams) was taken and 10 grams of silanated glass from example 2 fraction B was mixed in using the procedure as given in example 3. This paste contained a total of 88.0% filler. The properties were measured and results are given in Table 1.

EXAMPLE 8

Preparation of a First Paste Containing Additional Filler Fraction A

UK221511

One hundred grams of the paste from example 1 was taken and mixed at 50° C. with 158.3 grams of silanated glass fraction A from example 2 using a planetary mixer. After mixing for 15 minutes the paste had formed a coherent mass. This was cut up and was spread around the mixing pot before being mixed for a further 15 minutes. The paste mass was again cut up, spread around the pot and mixed for 15 minutes, but this time a vacuum of 220 mbar was applied for the last 10 minutes. The paste contained a total of 90% filler, but was judged to be too dry and stiff. A further 10 grams of the paste from example 1 was therefore added and the mixing procedure outlined above repeated. The resulting paste contained a total of 89.6% filler by weight. The properties of the paste were measured and these are given in Table 1.

EXAMPLE 9

Preparation of a Second Paste Containing Additional Filler Fraction A

UK221541

The paste from example 6 (233.7 grams) was taken and warmed to 50° C. in a planetary mixer. Silanated fraction A from example 2 (10.31 grams) was added and the mixing procedure carried out as outlined in example 3. This paste contained a total of 89% filler. The properties of the paste were measured and these are given in Table 1.

EXAMPLE 10

Preparation of a Third Paste Containing Additional Filler Fraction A

UK221542

The paste from example 7 (199 grams) was taken and warmed to 50° C. in a planetary mixer. Silanated fraction A from example 2 (14.96 grams) was added and the mixing procedure carried out as outlined in example 3. This paste contained a total of 88.6% filler. The properties of the paste were measured and these are given in Table 1.

EXAMPLE 11

Preparation of a Paste Containing an Additional Filler Fraction with Spherical Particles

UK221671

Spherical glass beads with a particle size ranging from 40 to 70 microns and a particle size span of about 0.5 were silanated by slurrying them at room temperature with a solution of 3-(trimethoxysilyl)propyl methacrylate (1% of the weight of the glass) in water acidified with acetic acid. After one hour the glass spheres were filtered off and dried for 36 hours at 85° C. in an oven. Two hundred grams of the paste from example 1 were mixed with two hundred and twenty two grams of these silanated spheres following the procedure in example 3. The resulting paste felt only marginally stiffer than the paste from example 3 even though it contained an extremely high total solid filler content of 88%. The properties were measured and the results are given in Table 1. It is notable that the Shore A hardness value of this paste was only 3 units higher than that of the starting paste, even though the solid filler content of the two pastes differed by 13%.

EXAMPLE 12

Preparation of a Second Paste Containing an Additional Filler Fraction with Spherical Particles

UK221681

The paste from example 11 (382 grams) was mixed as described in example 3 with further silanated glass spheres (34.4 grams). The result was a stiff paste which was nevertheless easily spatulated and clinically adaptable to a tooth surface. The properties were measured and the results are given in Table 1.

EXAMPLE 13

Preparation of a Second Paste Containing an Additional Filler Fraction with Both Spherical and Irregular Shaped Particles

UK221722

The filler fraction B was mixed with an equal weight of the spherical filler as used in example. A paste was produced containing 88.5% total weight percent filler, using the method as in example 3. The properties are given in Table 1.

EXAMPLE 14

Preparation of a Third Paste with an Additional Fraction Comprising Spherical Particles with a Narrow Particle Size Distribution Spherical glass beads with a mean size of 25.2 microns, a D(v, 0.9) of 36.2 microns, and a D(v, 0.1) of 16.8 microns (span=0.8) were silanated as in example 11. These spheres were mixed in a planetary mixer with the resin mixture as in example 1 (13.2 parts), glass powder with a mean particle size of 0.8 microns (36.8 parts) and strontium fluoride with a mean particle size of 0.8 microns (2.7 parts) until a homgenous paste was obtained. The properties were measured and are given in the table.

EXAMPLE 15

Preparation of a Fourth Paste with an Additional Fraction Comprising Spherical Particles with a Narrow Particle Size Distribution Spherical glass beads with a mean size of 17.7 microns, a D(v, 0.9) of 29.6 microns, and a D(v, 0.1) of 10.4 microns (span=1.08) were silanated as in example 11. These spheres were mixed in a planetary mixer with the resin mixture as in example 1 (13.6 parts), and glass powder with a mean particle size of 0.8 microns (37.95 parts) until a homgenous paste was obtained. The properties were measured and are given in the table.

COMPARATIVE EXAMPLE 1

Using Additional Filler with a Wide Particle Size Distribution

UK221631

The glass powder used in example 2 was taken and passed through a 250 micron sieve to remove coarse particles. When the particle size was measured using a Malvern Mastersizer S 2.10 the mean size was found to be 39.3 microns with a D(0.9) of 132.4 and a D(0.1) of 2.0 microns, corresponding to a span of 3.3. This was silanated as described in example 2. The silanated glass powder (100 grams) was added to the paste from example 1 (200 grams) using the mixing procedure described previously in example 3. The resulting paste contained a total of 83.1% filler and was a very stiff paste. A further 10 grams of the silanated glass powder above was added and the mixing procedure repeated. The resulting paste contained a total of 83.7% filler and was dry, crumbly and only just coherent. It was not possible to add more glass and still obtain a cohesive paste. The properties were measured and results are given in Table 1. This paste was very stiff and could not be extruded from a dental syringe.

Measurement of Extrusion Force

Dental syringes (Hawe-Neos Dental, CH-6934 Bioggio, Switzerland, article number 436) with an internal tip diameter of 2 mm were filled with the material to be tested. After allowing the syringe and contents to equilibrate to 23° C., the syringes were mounted in a universal testing machine (Zwick) and the material extruded by pushing the piston into the syringe at a constant velocity of 28 mm per minute. The force on the piston, or extrusion force, was noted. At least three measurements for each material were taken and the average extrusion force was calculated. Further syringes were tested by hand, and the ability to extrude the paste from the syringe judged from the hand force needed.

Measurement of Yield Strength

Metal forms with an internal diameter of 4 mm and a height of 6 mm as described in ISO 9917 section 7.4 were used to prepare the specimens. The paste to be measured was filled into the forms, covered with polyester foil, and pressed with metal plates to extrude excess material. The material was then cured for 40 seconds from each end using a dental curing lamp (Spectrum Lite, Dentsply) with an output between 600 and 700 mW/cm$^2$. The forms complete with specimen were drawn across silicon carbide paper (600 grit) until a smooth surface level with the end of the form was obtained, and then the cured specimens were removed from the form. The specimens were stored in water at 37° C. for 24 hours before being tested in a universal testing machine (Zwick) with a crosshead speed of 1 mm/minute. The stress strain curve for each specimen was inspected and found to consist essentially of an initial straight portion followed by a curved portion leading to the final breaking point. The straight portion of the curve corresponds to elastic behaviour of the material, whereas the curved portion corresponds to plastic flow. The force at which the stress strain curve first deviated from a straight line was taken as the yield point. The yield point is expressed in MPa, and is calculated by dividing the yield force in Newtons by the cross-sectional area of the specimen. The average value of at least five specimens for each material was calculated.

Properties of the Pastes

TABLE 1

| Material from example | % filler | Yield str. MPa | Vickers hardness HV5 | Shrinkage volume % | Additional filler D(v, 0.5) and span | Extrusion force Newtons | Extrusion by hand |
|---|---|---|---|---|---|---|---|
| 1 | 74.7 | 154.4 | 63.7 | 2.6 | none | 92 | Easily extrudable |
| 3 (UK221581) | 86.0 | 200.0 | 78.9 | 1.6 | 60, 1.26 | | Extrudable |
| 4 (UK221591) | 86.5 | 200.0 | 87.2 | | 60, 1.26 | | Extrudable |
| 5 (UK221592) | 87.0 | 203.9 | 95.6 | 1.5 | 60, 1.26 | 290 | Extrudable |

TABLE 1-continued

| Material from example | % filler | Yield str. MPa | Vickers hardness HV5 | Shrinkage volume % | Additional filler D(v, 0.5) and span | Extrusion force Newtons | Extrusion by hand |
|---|---|---|---|---|---|---|---|
| 6 (UK221593) | 87.5 | 205.2 | 95.7 |  | 60, 1.26 |  | Extrudable but stiff |
| 7 (UK221611) | 88.0 | 215.6 | 94.5 | 1.4 | 60, 1.26 |  | Extrudable but stiff |
| 8 (UK221511) | 89.6 | 198.0 | 77.0 | 1.1 | 175, 0.9 |  | Not extrudable |
| 9 (UK221541) | 89.0 | 197.0 | 68.6 |  | 175, 0.9 |  | Not extrudable |
| 10 (UK221542) | 88.6 | 195.0 | 67.9 | 1.3 | 175, 0.9 |  | Just extrudable |
| 11 (UK221671) | 88.0 | 188.4 | 71.5 |  | 175, 0.9 | 120 | Easily extrudable |
| 12 (UK221681) | 89.0 | 191.1 | 62.4 |  | 175, 0.9 |  | Easily extrudable |
| 13 (UK221722) | 88.5 | 192.3 |  | 1.2 | 175, 0.9 |  | Easily extrudable |
| 14 (UK25-61-1) | 86.8 | 187 | 87.0 | 1.5 | 25.2, 0.8 | 130 | Easily extrudable |
| 15 (GB8-114-1) | 86.7 | 223 | 91.0 | 1.6 | 17.7, 1.08 | 65 | easily extrudable |
| Comparative example 1 (UK221631) | 83.7 | 205.0 | 68.3 | 1.8 | 39.3, 3.3 | >500 | Not extrudable |

From Table 1 it can be seen that the conventional paste of example 1 has a yield strength of only 154 MPa, a Vickers hardness of 63.7, a volume shrinkage of 2.6%, and an extrusion force from a dental syringe of 92 Newtons. This paste may therefore be easily extruded from a dental syringe, but has an unacceptably high shrinkage as well as low surface hardness and low yield strength.

When the filler loading is increased by adding additional filler with a conventional broad particle size distribution with a span of 3.3 as in comparative example 1, the yield strength is improved and the shrinkage is reduced below 2%, but the surface hardness is barely changed and the paste becomes so stiff that it can no longer be extruded from a dental syringe. In contrast the formulations from examples 3, 4, 5, 6, 7, 14, and 15 which fall within the scope of the present invention have improved yield strengths, improved surface hardness, reduced volume shrinkage, and are also extrudable from a dental syringe.

The present invention therefore allows the formulation of pastes with required optimum properties of yield strength, surface hardness and extrudability from a dental syringe, which are not otherwise possible. Different methods of particle size measurement give different results, and the values given for purposes of the present invention are determined by sieving or by use of a malvern mastersizer s version 2,10 laser diffraction particle size analyser

What is claimed is:

1. An intra-oral or extra-oral dental restorative material comprising:
   a) at least one polymerisable monomer
   b) a first solid filler component with a mean particle size between 0.1 and 5 microns
   c) a second solid filler component with a mean particle size at least ten times greater than the mean particle size of the first solid filler component and a particle size span of less than 1.5.

2. An intra-oral or extra-oral dental restorative material comprising:
   a) at least one polymerisable monomer
   b) a first solid filler component with a mean particle size between 0.1 and 5 microns
   c) a second solid filler component with a mean particle size at least twenty times greater than the mean particle size of the first solid filler component and a particle size span of less than 1.5.

3. A material as in claim 1 in which the particle size span of the second filler is less than 1.3.

4. A material as in claim 2 in which the particle size span of the second filler is less than 1.3.

5. A material as in claim 1 in which 70 percent of the particles in the second filler component are within the range of 75 to 125 percent of its mean size.

6. A material as in claim 1 in which 80 percent of the particles in the second filler component are within the range of 75 to 125 percent of its mean size.

* * * * *